United States Patent
Pacetti et al.

(12) 
(10) Patent No.: US 6,565,659 B1
(45) Date of Patent: May 20, 2003

(54) STENT MOUNTING ASSEMBLY AND A METHOD OF USING THE SAME TO COAT A STENT

(75) Inventors: Stephen D. Pacetti, San Jose, CA (US); Plaridel K. Villareal, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/896,436

(22) Filed: Jun. 28, 2001

(51) Int. Cl.[7] .............................................. B05C 13/02
(52) U.S. Cl. ...................... 118/500; 118/504; 118/505; 623/1.46; 623/1.47; 623/1.48; 606/194
(58) Field of Search .................................. 118/500, 504, 118/505; 623/1.46, 1.47, 1.48; 427/2.24, 2.25, 2.28, 2.3; 606/194

(56) References Cited

U.S. PATENT DOCUMENTS

| | | | |
|---|---|---|---|
| 4,733,665 A | | 3/1988 | Palmaz |
| 4,800,882 A | | 1/1989 | Gianturco |
| 4,886,062 A | | 12/1989 | Wiktor |
| 5,234,457 A | * | 8/1993 | Andersen ..................... 606/154 |
| 5,897,911 A | | 4/1999 | Loeffler ...................... 427/2.25 |
| 5,935,135 A | * | 8/1999 | Bramfitt et al. ............. 606/191 |
| 6,156,373 A | * | 12/2000 | Zhong et al. .............. 427/2.28 |

* cited by examiner

Primary Examiner—Laura Edwards
(74) Attorney, Agent, or Firm—Squire, Sanders & Dempsey LLP

(57) ABSTRACT

A stent mounting device and a method of coating a stent using the device are provided.

22 Claims, 3 Drawing Sheets

STENT MOUNTING ASSEMBLY AND A METHOD OF USING THE SAME TO COAT A STENT

BACKGROUND OF THE INVENTION

1. Field of the Invention

This invention relates to a stent mounting device and a method of coating a stent using the device.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the coating from the stent and leaving bare areas. Alternatively, the excess coating may stick to the stent, thereby leaving excess coating as clumps or pools on the struts or webbing between the struts.

Thus, it is desirable to minimize the amount of coating material that is deposited on the interface between the stent and the apparatus supporting the stent during the coating process to minimize coating defects. Accordingly, the present invention provides for a device for supporting a stent during the coating application process. The invention also provides for a method of coating the stent supported by the device.

SUMMARY OF THE INVENTION

The present invention provides an apparatus for supporting a stent. The apparatus includes a mounting assembly for supporting a stent during a process of applying a coating substance to the stent. The mounting assembly prevents the formation of the coating or at least minimizes the amount or thickness of the coating that can be formed on the regions of the stent where the mounting assembly is in contact with the stent.

In one embodiment, the mounting assembly includes a mounting member for supporting the stent and a shield member for providing a barrier between a selected area of the stent and a coating applicator. In another embodiment, the mounting assembly includes a first member for supporting the stent at a first end, a second member for supporting the stent at a second end, a third member connecting the first member to the second member and extending through the longitudinal bore of the stent, and a shield member for providing a barrier between a selected area of the stent and a coating applicator.

In still another embodiment, the mounting assembly includes a shielding member capping over one end of the stent without being in contact with the surface of the stent. In another embodiment, the mounting assembly includes a mounting member for supporting the stent and a shield member supported by the mounting member for creating a barrier between a portion of the stent and a coating applicator. In such an embodiment, the position of the shield member on the mounting member can be adjusted so as to allow a user to modify the area over which the shield member covers the stent.

In yet another embodiment, the mounting assembly includes a first member having a first coning end that can be at least partially inserted within a first end of the stent and a second member having a second coning end that can be at least partially inserted within an opposing second end of the stent, the coning ends being in contact with the ends of the stent. In such an embodiment, the mounting assembly further includes a third member connecting the first member to the second member and shielding members supported by the first and second members for reducing or eliminating the amount of the coating substance that is applied to the first and second ends of the stent.

Also provided is an assembly for supporting a stent during the coating process. The assembly includes means for minimizing or eliminating the amount of coating material that can be applied to a designated area of the stent during the coating process. In one embodiment, the means is defined by a hollow body capable of surrounding a region of the stent without being in contact with the surface of the stent. In another embodiment, the amount of coating material can be minimized or eliminated at the regions where the stent is in contact with the assembly.

The present invention additionally provides a method of coating a stent. The method includes mounting a stent on a support assembly, wherein the support assembly is configured to reduce or eliminate the amount of coating that is applied to the regions where the stent is in contact with the support assembly. The method also includes applying a coating material to the stent for forming a coating.

In one embodiment, the act of applying includes spraying the coating material onto the stent. In another embodiment, the act of applying a coating includes applying the coating material to a stent while rotating the stent about the longitudinal axis of the stent. In another embodiment, the act of applying a coating includes applying the coating material to a stent while moving the stent in a linear direction about the longitudinal axis of the stent.

DETAILED DESCRIPTION

Embodiments of the Mounting Assembly

Figure 1:
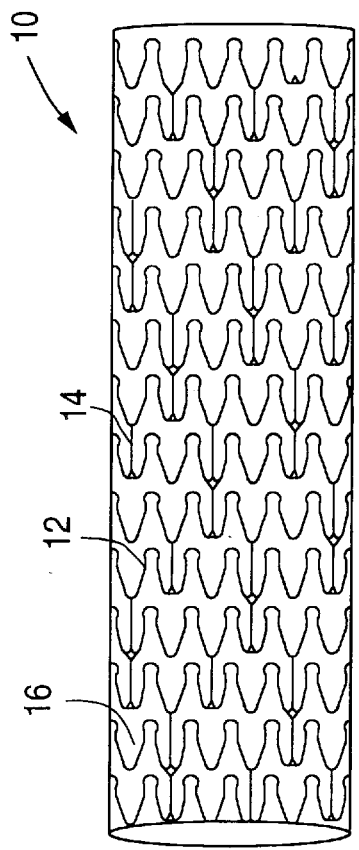
FIG. 1 illustrates a conventional stent.
Figure 2A:
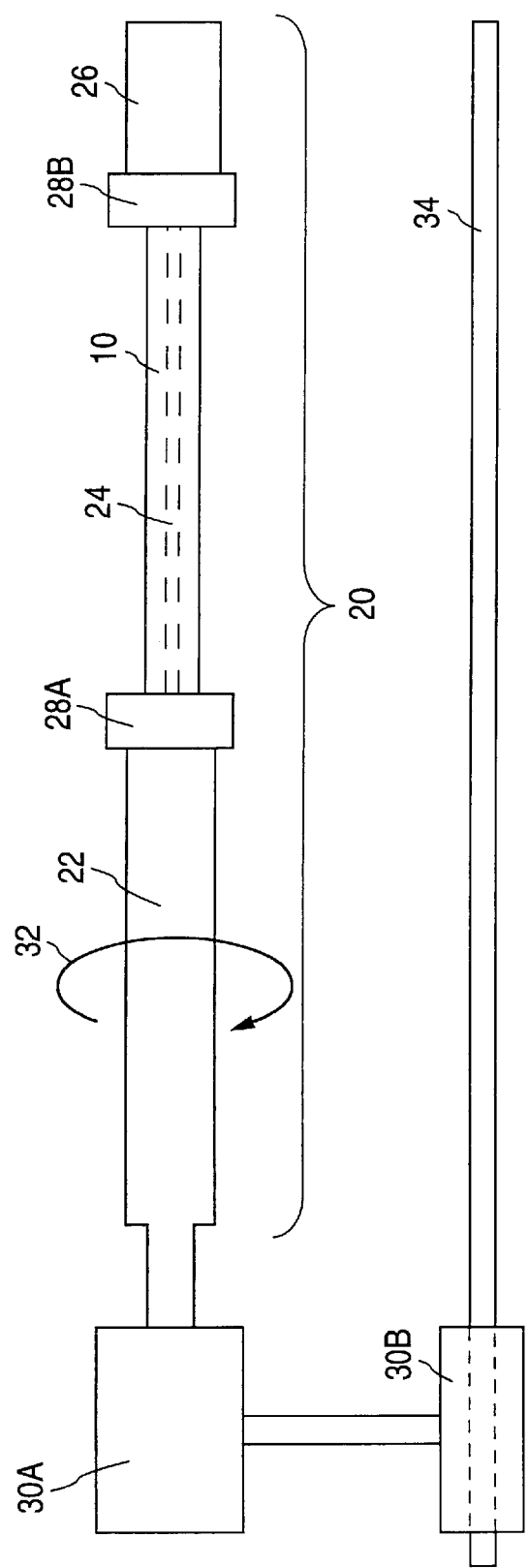
FIG. 2A illustrates a mounting assembly for supporting a stent.

Referring to FIG. 2A, a mounting assembly 20 for supporting stent 10 is illustrated to include a support member 22, a mandrel 24, a lock member 26, and shields 28A and 28B. Support member 22 can connect to a motor 30A so as to provide rotational motion about the longitudinal axis of stent 10, as depicted by arrow 32, during the coating process. Another motor 30B can also be provided for moving support member 22 in a linear direction, back and forth, along a rail 34.

Figure 2B:
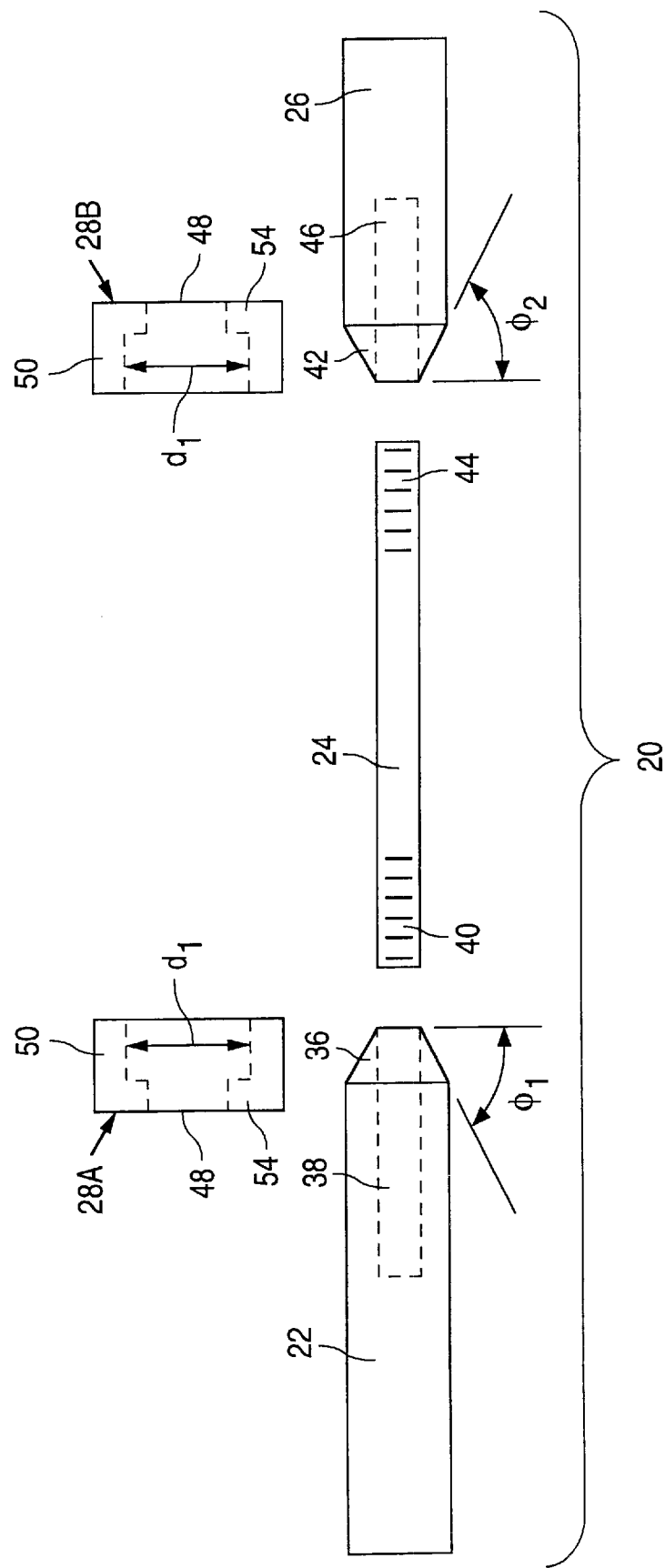
FIG. 2B illustrates an expanded view of the mounting assembly in accordance with one embodiment of the present invention.

Referring to FIG. 2B, support member 22 includes a coning end portion 36, tapering inwardly at an angle $\phi_1$ of about 15° to about 75°, more narrowly from about 30° to about 60°. By way of example, angle $\phi_1$ can be about 45°. In accordance with one embodiment, mandrel 24 can be permanently affixed to coning end portion 36. Alternatively, support member 22 can include a bore 38 for receiving a first end 40 of mandrel 24. First end 40 of mandrel 24 can be threaded to screw into bore 38 or, alternatively, can be retained within bore 38 by a friction fit. Bore 38 should be deep enough so as to allow mandrel 24 to securely mate with support member 22. The depth of bore 38 can also be over-extended so as to allow a significant length of mandrel 24 to penetrate or screw into bore 38. Bore 38 can also extend completely through support member 22. This would allow the length of mandrel 24 to be adjusted to accommodate stents of various sizes.

The outer diameter of mandrel 24 can be smaller than the inner diameter of stent 10 so as to prevent the outer surface of mandrel 24 from making contact with the inner surface of stent 10. A sufficient clearance between the outer surface of mandrel 24 and the inner surface of stent 10 should be provided to prevent mandrel 24 from obstructing the pattern of the stent body during the coating process. By way of example, the outer diameter of mandrel 24 can be from about 0.010 inches (0.254 mm) to about 0.017 inches (0.432 mm) when stent 10 has an inner diameter of between about 0.025 inches (0.635 mm) and about 0.035 inches (0.889 mm).

Lock member 26 includes a coning end portion 42 having an inwardly tapered angle $\phi_2$. Angle $\phi_2$ can be the same as or different than the above-described angle $\phi_1$. A second end 44 of mandrel 24 can be permanently affixed to lock member 26 if end 40 is disengagable from support member 22. Alternatively, in accordance with another embodiment, mandrel 24 can have a threaded second end 44 for screwing into a bore 46 of lock member 26. Bore 46 can be of any suitable depth that would allow lock member 26 to be incrementally moved closer to support member 22. Bore 46 can also extend completely through lock member 26. Accordingly, stents 10 of any length can be securely pinched between support and lock members 22 and 26. In accordance with yet another embodiment, a non-threaded second end 44 and bore 46 combination is employed such that second end 44 can be press-fitted or friction-fitted within bore 46 to prevent movement of stent 10 on mounting assembly 20.

Figure 3:
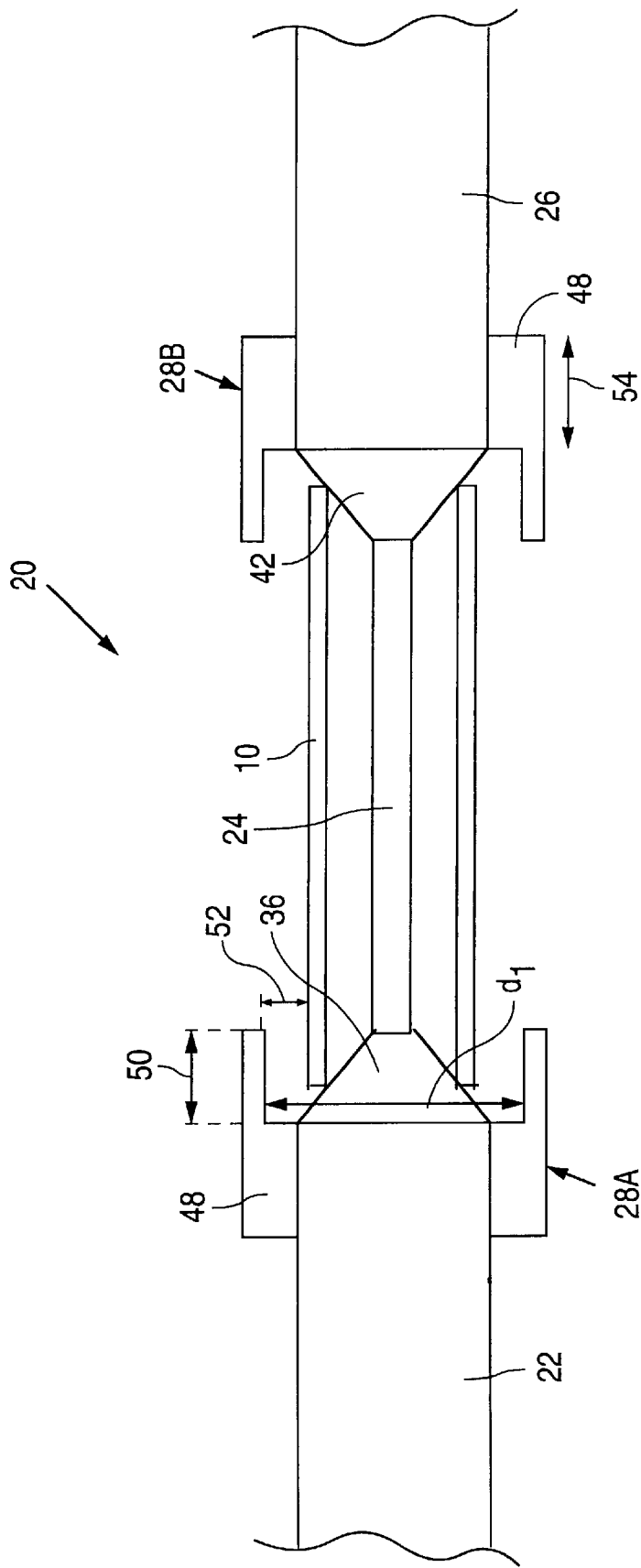
FIG. 3 is a cross-sectional view of the interface between the mounting assembly and the stent.

Mounting assembly 20 supports stent 10 via coning end portions 36 and 42. FIG. 3 illustrates the interface between coning end portions 36 and 42 and the opposing ends of stent 10 so as to provide minimal contact between stent 10 and mounting assembly 20. Opposing forces exerted from support and lock members 22 and 26, for securely pinching stent 10, should be sufficiently strong so as to prevent any significant movement of stent 10 on mounting assembly 20. However, the exerted force should not compress stent 10 so as to distort the body of stent 10. Over or under application of support force can lead to coating defects, such as non-uniformity of the coating thickness.

Shields 28A and 28B provide a circumferential barrier around the peripheral ends of stent 10, particularly over the area where stent 10 is in physical contact with coning end portions 36 and 42. Shields 28A and 28B can be permanently affixed to support member 22 and/or lock member 26. Alternatively, in a more useful commercial embodiment, shields 28A and 28B can be adjustably supported by members 22 and/or 26.

In one embodiment, shields 28A and 28B can be defined by a hollow body 48 having a first section or overhang 50 that is configured to extend over at least a portion of stent 10. Overhang 50 should have an inner diameter $d_1$ that is larger than the outer diameter of stent 10, in a mount position on mounting assembly 20, so as to create a sufficient gap 52 between shields 28A and 28B and the outer surface of stent 10 for eliminating any contact with the deposited coating. Gap 52 can be from about 0.003 inches (0.08 mm) to about 0.08 inches (about 2.03 mm), typically about 0.04 inches (about 1.02 mm), in measurement. Care should be taken, however, to ensure that gaps 52 are not so large as to allow the composition to access the stent 10-mounting assembly 20 interface.

Hollow body 48 can also include a second section 54 for adjustably receiving the non-coned portions of members 22 and 26. For example, second section 54 and non-coned portions of support and lock members 22 and 26 can be threaded such that the clockwise or counterclockwise rotation of shields 28A and 28B would allow the user to move shields 28A and 28B towards or away from stent 10. Thus, the area over stent 10 that is sheltered by overhang 50 can be adjusted. Hollow body 48 and second section 54 can also be integral parts of the non-coned portions of support and lock members 22 and 26.

Shields 28A and 28B function to minimize coating defects at the ends of stent 10 by limiting or eliminating the application of the coating substance to the ends of stent 10. The presence of shields 28A and 28B causes the coating to be thinner (or completely eliminated) on the surface of stent 10 over which shields 28A and 28B are hung, as compared to the surface of stent 10 that is not screened by shields 28A and 28B. Accordingly, the area of stent 10 over which shields 28A and 28B are extended should be selected to yield a suitable balance between reduction of the potential for coating defects at the ends of stent 10 and uniformity of the coating thickness. Further, appropriate selection of gap 52 and overhang 50, taking into account the distance between the spray nozzle and stent 10, can facilitate a gradual decrease in the coating thickness at the ends of stent 10 beneath overhang 50 as opposed to an abrupt void of coating near the shielded stent ends.

Coating a Stent Using the Mounting Assembly

The following method of application is being provided by way of illustration and is not intended to limit the embodiments of mounting assembly 20 of the present invention. A spray apparatus, such as EFD 780S spray device with VALVEMATE 7040 control system (manufactured by EFD Inc., East Providence, RI), can be used to apply a composition to a stent. EFD 780S spray device is an air-assisted external mixing atomizer. The composition is atomized into small droplets by air and uniformly applied to the stent surfaces. The atomization pressure can be maintained at a range of about 5 psi to about 20 psi. The droplet size depends on such factors as viscosity of the solution, surface tension of the solvent, and atomization pressure. Other types of spray applicators, including air-assisted internal mixing atomizers and ultrasonic applicators, can also be used for the application of the composition.

During the application of the composition, a stent supported by mounting assembly 20 can be rotated about the stent's central longitudinal axis. Rotation of the stent can be from about 1 rpm to about 300 rpm, more narrowly from about 50 rpm to about 150 rpm. By way of example, the stent can rotate at about 120 rpm. The stent can also be moved in a linear direction along the same axis. The stent can be moved at about 1 mm/second to about 12 mm/second, for example about 6 mm/second, or for a minimum of at least two passes (i.e., back and forth past the spray nozzle). The flow rate of the solution from the spray nozzle can be from about 0.01 mg/second to about 1.0 mg/second, more narrowly about 0.1 mg/second. Multiple repetitions for applying the composition can be performed, wherein each repetition can be, for example, about 1 second to about 10 seconds in duration. The amount of coating applied by each repetition can be about 0.1 micrograms/cm$^2$ (of stent surface) to about 10 micrograms/cm$^2$, for example less than about 2 micrograms/cm$^2$ per 5-second spray.

Each repetition can be followed by removal of a significant amount of the solvent(s). Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2–4 hours) or by the application of warm air. The application of warm air between each repetition minimizes coating defects and minimizes interaction between the active agent and the solvent. The temperature of the warm air can be from about 30° C. to about 60° C., more narrowly from about 40° C. to about 50° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds. Any suitable number of repetitions of applying the composition followed by removing the solvent(s) can be performed to form a coating of a desired thickness or weight. Excessive application of the polymer in a single repetition can, however, cause coating defects.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

In accordance with one embodiment, the stent can be at least partially pre-expanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

In accordance with one embodiment, the composition can include a solvent and a polymer dissolved in the solvent and optionally a wetting fluid. The composition can also include active agents, radiopaque elements, or radioactive isotopes. Representative examples of polymers that can be used to coat a stent include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly (hydroxybutyrate); poly(hydroxybutyrate-co-valerate); polydioxanone; polyorthoester; polyanhydride; poly (glycolic acid); poly(D,L-lactic acid); poly(glycolic acid-co-trimethylene carbonate); polyphosphoester; polyphosphoester urethane; poly(amino acids); cyanoacrylates; poly (trimethylene carbonate); poly(iminocarbonate); copoly (etheresters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformnamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

Wetting fluid can be used to enhance the wetting of the composition or to increase the capillary permeation of the composition. Capillary permeation is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. Representative examples of wetting fluid include tetrahydrofuran (THF), dimethylformamide (bMF), 1-butanol, and n-butyl acetate.

The active agent could be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone. Exposure of the active ingredient to the composition should not adversely alter the active ingredient's composition or characteristic. Accordingly, the particular active ingredient is selected for compatibility with the solvent or blended polymer-solvent.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An apparatus for supporting a stent, comprising:
   a mounting assembly for supporting a stent during a process of applying a coating substance to the stent, wherein the mounting assembly prevents formation of the coating or at least minimizes an amount or thickness of the coating that can be formed on regions of the stent where the mounting assembly is in contact with the stent,
   wherein the mounting assembly comprises:
      a first member for supporting the stent at a first end;
      a second member for supporting the stent at a second end;
      a third member connecting the first member to the second member and extending through a longitudinal bore of the stent; and
      a shielding member for providing a barrier between a selected area of the stent and a coating applicator.

2. The apparatus of claim 1, wherein the first member has a first coning end and the second member has a second coning end.

3. The apparatus of claim 1, wherein the shielding member caps over at least one of the first and second ends of the stent without being in contact with a surface of the stent.

4. The apparatus of claim 1, wherein the shielding member is rotatably connected to the first member such that rotation of the shielding member moves the shielding member relative to the stent.

5. An apparatus for supporting a stent, comprising:
   a mounting assembly for supporting a stent during a process of applying a coating substance to the stent, wherein the mounting assembly prevents formation of the coating or at least minimizes an amount or thickness of the coating that can be formed on regions of the stent where the mounting assembly is in contact with the stent,
   wherein the mounting assembly comprises:
      at least one mounting member for supporting the stent; and
      a shielding member supported by the at least one mounting member for creating a barrier between a portion of the stent and a coating applicator, and wherein the position of the shielding member on the at least one mounting member can be adjusted so as to allow a user to modify an area over which the shielding member covers the stent.

6. The apparatus of claim 5, wherein the shielding member caps over one end of the stent without being in contact with the surface of the stent.

7. An apparatus for supporting a stent, comprising:

a mounting assembly for supporting a stent during a process of applying a coating substance to the stent, wherein the mounting assembly prevents formation of the coating or at least minimizes an amount or thickness of the coating that can be formed on regions of the stent where the mounting assembly is in contact with the stent, wherein the mounting assembly comprises:

a first member having a first coning end that can be at least partially inserted within a first end of the stent;

a second member having a second coning end that can be at least partially inserted within an opposing second end of the stent, the coning ends being in contact with the ends of the stent; and shielding members supported by the first and second members for reducing or eliminating the amount of the coating substance that is applied to the first and second ends of the stent.

8. The apparatus of claim 7, further comprising a third member connecting the first member to the second member.

9. The apparatus of claim 7, wherein the shielding members are rotatably connected to the first and second members such that rotation of the shielding members moves the shielding members relative to the stent.

10. An assembly for supporting a stent during a coating process, comprising:

first supporting means for supporting the stent at a first end;

second supporting means for supporting the stent at a second end; and means for minimizing or eliminating an amount of coating material that can be applied to a designated area of the stent during the coating process, wherein the means for minimizing or eliminating creates a barrier between a portion of the stent and a coating applicator.

11. The assembly of claim 10, wherein the means for minimizing or eliminating is defined by a hollow body capable of surrounding a region of the stent without being in contact with the surface of the stent.

12. The assembly of claim 11, wherein the hollow body comprises a first section extending over at least a portion of the stent, and a second section.

13. The assembly of claim 12, wherein the first section of the hollow body has an inner diameter larger than an outer diameter of the stent, so as to create a gap between the hollow body and the stent for eliminating any contact with the coating material deposited on the stent.

14. The assembly of claim 12, wherein the second section is adjustably moved so as to modify an area over which the first section extends over the stent.

15. The assembly of claim 10, wherein the means for minimizing or eliminating minimizes or eliminates the amount of coating material at regions where the stent is in contact with the assembly.

16. The assembly of claim 10, wherein the first supporting means has a first coning end and the second supporting means has a second coning end.

17. The assembly of claim 10, wherein the assembly further comprises connecting means for connecting the first supporting means to the second supporting means and extending through a longitudinal bore of the stent.

18. The assembly of claim 17 wherein the connecting means comprises a threaded end for screwing into a bore of the second supporting means.

19. An assembly for supporting a stent during application of a coating composition on the stent, the assembly comprising:

a body for being at least partially inserted into one end of a stent for supporting the stent during application of a coating composition;

a supporting member receiving a first end of the body; and a shielding member adjustably supported by the supporting member for allowing a user to selectively cover a region of the stent so as to minimize or eliminate the application of the coating composition to the region of the stent covered by the shielding member.

20. The assembly of claim 19, wherein the shielding member is rotatably supported by the supporting member such that a user can adjust a position of the shielding member by rotating the shielding member.

21. The assembly of claim 20, wherein the shielding member threadably receives the supporting member such that the rotation of the shielding member allows the user to move the shielding member relative to the stent.

22. The assembly of claim 19, wherein the body comprises a mandrel having an outer diameter smaller than an inner diameter of the stent so as to prevent contact between an outer surface of the mandrel and an inner surface of the stent.

* * * * *